(12) United States Patent
Toma et al.

(10) Patent No.: US 7,655,812 B2
(45) Date of Patent: Feb. 2, 2010

(54) PREPARATION OF DIMETHYLCHLOROSILANE

(75) Inventors: Toshihiro Toma, Annaka (JP); Koichiro Kobayashi, Annaka (JP); Yukinori Satou, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 20 days.

(21) Appl. No.: 12/034,008

(22) Filed: Feb. 20, 2008

(65) Prior Publication Data

US 2008/0200710 A1    Aug. 21, 2008

(30) Foreign Application Priority Data

Feb. 21, 2007    (JP)    ............................. 2007-040256

(51) Int. Cl.
*C07F 7/04*    (2006.01)
(52) U.S. Cl. .................................... 556/466
(58) Field of Classification Search .................. 556/466
See application file for complete search history.

(56) References Cited

U.S. PATENT DOCUMENTS

| | | | |
|---|---|---|---|
| 5,502,230 A * | 3/1996 | Mautner et al. | 556/468 |
| 6,271,407 B1 * | 8/2001 | Colin et al. | 556/468 |
| 6,939,984 B2 * | 9/2005 | Straussberger | 556/466 |

FOREIGN PATENT DOCUMENTS

| | | |
|---|---|---|
| JP | 54-9228 A | 1/1979 |
| JP | 8-81477 A | 3/1996 |

OTHER PUBLICATIONS

R. Calas et al., Journal of Organometallic Chemistry, vol. 225, pp. 117-130 (1982).

* cited by examiner

*Primary Examiner*—Daniel M Sullivan
*Assistant Examiner*—Chukwuma O Nwaonicha
(74) *Attorney, Agent, or Firm*—Birch, Stewart, Kolasch & Birch, LLP

(57) ABSTRACT

Dimethylchlorosilane is prepared by reacting 1,2-tetramethyldichlorodisilane with hydrogen chloride in the presence of a catalyst mixture of a) palladium, b) a tertiary amine, and c) a tertiary phosphine having at least one phenyl group having at least one functional group other than hydrogen. The catalyst does not lose its activity upon contact with hydrogen chloride at low temperatures and ensures production of dimethylchlorosilane in high yields.

7 Claims, No Drawings

PREPARATION OF DIMETHYLCHLOROSILANE

CROSS-REFERENCE TO RELATED APPLICATION

This non-provisional application claims priority under 35 U.S.C. §119(a) on Patent Application No. 2007-040256 filed in Japan on Feb. 21, 2007, the entire contents of which are hereby incorporated by reference.

TECHNICAL FIELD

This invention relates to a method for preparing dimethylchlorosilane, and more particularly, to a method for preparing dimethylchlorosilane by reacting 1,2-tetramethyldichlorodisilane with hydrogen chloride in the presence of a catalyst mixture of a) palladium, b) a tertiary amine, and c) a tertiary phosphine having at least one phenyl group having at least one functional group other than hydrogen.

BACKGROUND ART

In the direct synthesis of methylchlorosilanes by the Mueller-Rochow method from silicon and chloromethane at 250° to 300° C. using copper catalysts, disilanes are obtained as by-products. The main disilanes formed are 1,1,2,2-tetrachlorodimethyldisilane, 1,1,2-trichlorotrimethyldisilane, 1,1-dichlorotetramethyldisilane, 1,2-dichlorotetramethyldisilane, chloropentamethyldisilane, and hexamethyldisilane. Of these, 1,1,2,2-tetrachlorodimethyldisilane, 1,1,2-trichlorotrimethyldisilane, and 1,1-dichlorotetramethyldisilane can be cleaved into monosilanes by catalytic reaction with hydrogen chloride in the presence of tertiary amines or amides as described in R. Calas, J. Organometall. Chem., 225, 117, 1982. The main products formed are methyltrichlorosilane, dimethyldichlorosilane, and methyldichlorosilane.

However, 1,2-dichlorotetramethyldisilane cannot be cleaved using the above-mentioned catalyst and hydrogen chloride. JP-A 54-9228 describes the use of tetrakis(triphenylphosphine)palladium(0) as a catalyst for cleavage of 1,2-dichlorotetramethyldisilane, but space time yields of dimethylchlorosilane are very low. U.S. Pat. No. 5,502,230 or JP-A 8-81477 describes the use of a catalyst mixture of (A) palladium(0) or platinum(0) and (B) a tertiary amine, carboxylic amide, alkylurea, tertiary phosphine, phosphoric amide, quaternary ammonium halide or quaternary phosphonium halide, but space time yields of dimethylchlorosilanes are very low.

The tertiary phosphine used in Example of U.S. Pat. No. 5,502,230 is triphenylphosphine. It was recognized that when the temperature lowers below 90° C. in the presence of palladium and hydrogen chloride, triphenylphosphine forms trans-dichlorobistriphenylphosphine palladium(II), losing its catalytic activity. Then, the hydrogen chloride remaining at the end of reaction must be removed from the system before the system temperature is lowered.

However, the catalyst gradually loses its activity because complete removal of hydrogen chloride from the system is difficult. Another issue associated with the use of triphenylphosphine is that triphenyl phosphine is thermally decomposed, yielding a by-product, benzene. Benzene has a boiling point approximate to that of dimethyldichlorosilane which is also formed as a by-product separately from dimethylchlorosilane, so that separation of benzene from dimethyldichlorosilane is difficult. This requires a special separation means such as a multi-stage distillation column.

DISCLOSURE OF THE INVENTION

An object of the present invention is to provide a method for preparing dimethylchlorosilane that enables efficient cleavage of 1,2-tetramethyldichlorodisilane without a loss of catalytic activity over a long term, thus furnishing in high yields dimethylchlorosilane which is a monomeric raw material playing the important role in the silicone industry.

The inventors have found that when 1,2-tetramethyldichlorodisilane is reacted with hydrogen chloride in the presence of a catalyst mixture of a) palladium, b) a tertiary amine, and c) a tertiary phosphine having at least one phenyl group having at least one functional group other than hydrogen, dimethylchlorosilane can be produced in high yields without a loss of catalytic activity.

Accordingly, the invention provides a method for preparing dimethylchlorosilane of the formula: $H-Si-(CH_3)_2Cl$, comprising reacting 1,2-tetramethyldichlorodisilane with hydrogen chloride in the presence of a catalyst mixture of
  a) palladium,
  b) a tertiary amine, and
  c) a tertiary phosphine having at least one phenyl group having at least one functional group other than hydrogen.

Typical catalyst component a) is palladium with the oxidation state 0 or palladium (II) oxide in the form of metal alone or on a powder carrier.

BENEFITS OF THE INVENTION

The method of the invention has the advantages that the catalyst does not lose its activity even in contact with hydrogen chloride at low temperatures and that dimethylchlorosilane can be produced in high yields from 1,2-tetramethyldichlorodisilane.

DESCRIPTION OF THE PREFERRED EMBODIMENT

The method of the invention starts with the 1,2-tetramethyldichlorodisilane feed which may contain 1,1,2,2-tetrachlorodimethyldisilane, 1,1,2-trichlorotrimethyldisilane, 1,1-dichlorotetramethyldisilane, chloropentamethyldisilane, hexamethyldisilane, dimethyldichlorosilane, methyldichlorosilane, trichloromethylsilane, ethylmethyldichlorosilane, hydrocarbons, chlorinated hydrocarbons, siloxanes, and trisilanes. The content of 1,2-tetramethyldichlorodisilane should desirably be 60 to 80% by weight, and more desirably 60 to 100% by weight of the feed although contents above or below the range may be acceptable.

Hydrogen chloride to be reacted with 1,2-tetramethyldichlorodisilane should preferably be fed in gas form. The desired feed rate of hydrogen chloride is such that 1 to 4 moles, especially 1 to 2 moles of hydrogen chloride is available per mole of 1,2-tetramethyldichlorodisilane. Since hydrogen chloride is present in gas form at the relevant temperature and pressure, it can be readily separated from dimethylchlorosilane. Commercial hydrogen chloride may be used.

A catalyst mixture of a) palladium, b) a tertiary amine, and c) a tertiary phosphine is used in the reaction of 1,2-tetramethyldichlorodisilane with hydrogen chloride. The catalyst component a) is preferably palladium with the oxidation state 0 or palladium (II) oxide in the form of metal alone or on a powder carrier. More advantageous is the metal on a powder carrier.

The carrier material is advantageously an inorganic material free of other metal ingredients. Activated carbon is more advantageous. Thus the more advantageous catalyst component a) is palladium on activated carbon. The concentration of the metal (palladium) on the carrier is preferably 1 to 10% by weight, and more preferably 5 to 10% by weight based on the total weight of the metal and the carrier. Outside the range, too high metal concentrations may detract from catalytic activity, whereas too low metal concentrations may require larger charges of the catalyst component, reducing the efficiency of agitation.

The catalyst component b) is a tertiary amine, examples of which include tributylamine, trioctylamine, and triphenylamine.

The catalyst component c) is a tertiary phosphine having at least one phenyl group having at least one functional group other than hydrogen. Exemplary functional groups other than hydrogen include alkyl groups such as methyl, ethyl, and propyl, alkoxy groups such as methoxy, ethoxy and propoxy, and alkylene groups such as methylene. Exemplary phosphines include tritolylphosphine, tribenzylphosphine, and tris(methoxyphenyl)phosphine.

According to the invention, a combination of the above-mentioned catalyst components a), b), and c) is used in the reaction of 1,2-tetramethyldichlorodisilane with hydrogen chloride. This offers the advantages that the catalyst mixture does not lose its catalytic activity even when contacted with hydrogen chloride at low temperatures; that the reaction takes place effectively to form dimethylchlorosilane in high yields; and that separation of dimethyldichlorosilane by-product is easy. The preferred combination of catalyst components a), b), and c) is of metallic palladium on a carrier, tributylamine, and tritolylphosphine.

The catalyst component a) is preferably used in an amount of 0.0025 to 0.5% by weight, more preferably 0.0025 to 0.1% by weight, calculated as metallic palladium, based on the weight of the disilane charge. Outside the range, too less amounts of catalyst component a) may provide for a lower reactivity, which requires a longer time for reaction. Too much amounts of catalyst component a) may be uneconomical. The catalyst component b) is preferably used in an amount of at least 0.75% by weight, more preferably at least 1.5% by weight based on the weight of the disilane charge. The upper limit is not particularly set although the preferred amount is equal to or less than 5.0%, and more preferably equal to or less than 3.0% by weight.

The catalyst component c) is preferably used in an amount of at least 0.1% by weight, more preferably at least 0.2% by weight based on the weight of the disilane charge. The upper limit is not particularly set although the preferred amount is equal to or less than 1.0%, and more preferably equal to or less than 0.7% by weight.

The method of the invention can be carried out batchwise, semi-continuously or fully continuously. The reaction temperature is desirably in a range of 110 to 140° C., and advantageously 110 to 130° C. The reaction is preferably carried out in an atmosphere of an inert gas such as nitrogen or argon. Outside the range, too higher reaction temperatures may lead to reduced yields of dimethylchlorosilane because the dimethylchlorosilane formed can be dehydrogenated and converted into dimethyldichlorosilane. Too lower reaction temperatures may lead to inefficiency in that the reaction may not commence and more unreacted hydrogen chloride be released.

At the end of reaction, catalyst component a) can be readily separated from high-boiling residues, for example, by centrifugation or filtration.

EXAMPLE

Examples of the invention are given below by way of illustration and not by way of limitation.

Example 1

A 500-mL glass flask equipped with a distillation unit and a gas inlet tube for hydrogen chloride was charged with a catalyst composed of 2.0 g of 5% palladium on activated carbon, 1.3 g of tritolylphosphine, and 3.0 g of tributylamine, and 200 g of a disilane mixture composed mainly of 3.0 wt % of 1,1-tetramethyldichlorodisilane and 57.9 wt % of 1,2-tetramethyldichlorodisilane. With stirring in a nitrogen atmosphere under atmospheric pressure, the mixture was heated to 70° C. With stirring at 70° C., hydrogen chloride was fed at a rate of 10.8 L/hour. After a reaction time of 2 hours, no distillate collected.

After the reaction time of 2 hours, the hydrogen chloride feed was interrupted. With stirring in a nitrogen atmosphere under atmospheric pressure, the reaction mixture left in the flask was heated to 115° C. With stirring at 115° C., hydrogen chloride was fed again at a rate of 10.8 L/hour. The reaction product was distilled out of the top of the reaction flask, condensed, and analyzed by gas chromatography (GC-2010 by Shimadzu Mfg. Co., Ltd.). After a reaction time of 2 hours, there was collected 169.6 g of a distillate, which had the composition:

| | |
|---|---|
| dimethylchlorosilane | 31.4 wt %, |
| dimethyldichlorosilane | 55.5 wt %, |
| methyldichlorosilane | 1.8 wt %, and |
| trichloromethylsilane | 4.8 wt %. |

It was demonstrated that the catalyst did not lose its catalytic activity upon contact with hydrogen chloride at the low temperature, and after the temperature was raised to an appropriate level, it helped to form dimethylchlorosilane in high yields.

Comparative Example 1

A 500-mL glass flask equipped with a distillation unit and a gas inlet tube for hydrogen chloride was charged with a catalyst composed of 2.0 g of 5% palladium on activated carbon, 1.3 g of triphenylphosphine, and 1.5 g of tributylamine, and 200 g of a disilane mixture composed mainly of 5.0 wt % of 1,1-tetramethyldichlorodisilane and 69.7 wt % of 1,2-tetramethyldichlorodisilane. With stirring in a nitrogen atmosphere under atmospheric pressure, the mixture was heated to 90° C. With stirring at 90° C., hydrogen chloride was fed at a rate of 9.4 L/hour. After a reaction time of 2 hours, no distillate collected.

After the reaction time of 2 hours, the hydrogen chloride feed was interrupted. With stirring in a nitrogen atmosphere under atmospheric pressure, the reaction mixture left in the flask was heated to 130° C. With stirring at 130° C., hydrogen chloride was fed again at a rate of 11.4 L/hour. The reaction product was distilled out of the top of the reaction flask, condensed, and analyzed by gas chromatography (GC-14A by Shimadzu Mfg. Co., Ltd.). After a reaction time of 2 hours, there was collected 0.5 g of a distillate, which had the composition:

| | |
|---|---|
| dimethyldichlorosilane | 3.0 wt %, |
| trichloromethylsilane | 2.5 wt %, and |
| 1,2-tetramethyldichlorodisilane | 89.7 wt %. |

The desired compound, dimethylchlorosilane was not detected.

Comparative Example 2

A 500-mL glass flask equipped with a distillation unit and a gas inlet tube for hydrogen chloride was charged with a catalyst composed of 2.0 g of 5% palladium on activated carbon, 1.3 g of triphenylphosphine, and 1.5 g of tributylamine, and 200 g of a disilane mixture composed mainly of 5.0 wt % of 1,1-tetramethyldichlorodisilane and 69.7 wt % of 1,2-tetramethyldichlorodisilane. With stirring in a nitrogen atmosphere under atmospheric pressure, the mixture was heated to 90° C. With stirring at 90° C., hydrogen chloride was fed at a rate of 9.4 L/hour. After a reaction time of 2 hours, no distillate collected.

After the reaction time of 2 hours, the hydrogen chloride feed was interrupted. With stirring in a nitrogen atmosphere under atmospheric pressure, the reaction mixture left in the flask was cooled to 30° C. A catalyst composed of 2.0 g of 5% palladium on activated carbon, 1.3 g of triphenylphosphine, and 1.5 g of tributylamine was further added to the residual mixture. With stirring in a nitrogen atmosphere under atmospheric pressure, the mixture was heated again to 130° C. With stirring at 130° C., hydrogen chloride was fed again at a rate of 11.4 L/hour. The reaction product was distilled out of the top of the reaction flask, condensed, and analyzed by gas chromatography (GC-2010 by Shimadzu Mfg. Co., Ltd.). After a reaction time of 2 hours, there was collected 7.0 g of a distillate, which had the composition:

| | |
|---|---|
| dimethyldichlorosilane | 48.5 wt %, |
| methyldichlorosilane | 1.9 wt %, and |
| trichloromethylsilane | 22.6 wt %. |

It was demonstrated that contact with hydrogen chloride at low temperatures below 90° C. reduced a reactivity which could not be restored even by addition of a further catalyst, failing to produce the desired compound, dimethylchlorosilane.

Japanese Patent Application No. 2007-040256 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for preparing dimethylchlorosilane of the formula: $H-Si-(CH_3)_2Cl$, comprising reacting 1,2-tetramethyldichlorodisilane with hydrogen chloride in the presence of a catalyst mixture of
   a) palladium,
   b) a tertiary amine, and
   c) a tertiary phosphine of tritolylphosphine.

2. The method of claim 1, wherein catalyst component a) is palladium with the oxidation state 0 or palladium (II) oxide in the form of metal alone or on a powder carrier.

3. The method of claim 1, wherein catalyst component a) is palladium on activated carbon.

4. The method of claim 1, wherein the tertiary amine is selected from the group consisting of tributylamine, trioctylamine and triphenylamine.

5. The method of claim 1, wherein the catalyst mixture is a mixture of metallic palladium on a carrier, tributylamine and tritolylphosphine.

6. The method of claim 1, wherein the reacting step is carried out at a temperature of 110-140° C.

7. The method of claim 1, wherein the reacting step is carried out in an atmosphere of an inert gas.

* * * * *